(12) United States Patent
Nogueira

(10) Patent No.: US 10,408,724 B2
(45) Date of Patent: Sep. 10, 2019

(54) TORSION TESTING DEVICES AND METHODS

(71) Applicant: The Regents of the University of Colorado, Denver, CO (US)

(72) Inventor: Carnot L. Nogueira, Boulder, CO (US)

(73) Assignee: THE REGENTS OF THE UNIVERSITY OF COLORADO, Denver, CO (US)

( * ) Notice: Subject to any disclaimer, the term of this patent is extended or adjusted under 35 U.S.C. 154(b) by 121 days.

(21) Appl. No.: 15/825,150

(22) Filed: Nov. 29, 2017

(65) Prior Publication Data

US 2018/0149567 A1 May 31, 2018

Related U.S. Application Data

(60) Provisional application No. 62/427,676, filed on Nov. 29, 2016.

(51) Int. Cl.
| | |
|---|---|
| *G01N 3/00* | (2006.01) |
| *G01N 3/22* | (2006.01) |
| *G01N 3/04* | (2006.01) |
| *G01N 33/38* | (2006.01) |
| *G01N 3/24* | (2006.01) |

(52) U.S. Cl.
CPC .......... *G01N 3/22* (2013.01); *G01N 3/04* (2013.01); *G01N 33/383* (2013.01); *G01N 3/24* (2013.01); *G01N 2203/0025* (2013.01); *G01N 2203/0037* (2013.01); *G01N 2203/0266* (2013.01)

(58) Field of Classification Search
CPC .......... G01N 3/22; G01N 3/04; G01N 33/383; G01N 3/24; G01N 2203/0037; G01N 2203/0266
See application file for complete search history.

(56) References Cited

PUBLICATIONS

Helmick, C.G., Toker-Beeson, S., and Tanner J. E., Evaluation of Shear and Diagonal Tension in Plain Concrete, Concrete International, V. 38 (1), 2016, pp. 39-46.
Martin, L.H., Bending and torsion of plain concrete members, Building Science, V. 6 (4), 1971, pp. 253-265.
Chalioris, C. E., Karayannis, C. G., Experimental Validation of Smeared Analysis for Plain Concrete in Torsion, J Struct. Engnr, V. 126 (6), 2000.

*Primary Examiner* — Jamel E Williams
(74) *Attorney, Agent, or Firm* — FisherBroyles LLP; Anthony J. DoVale

(57) ABSTRACT

A torsional testing device for testing helical tensile strength, shear strength, and interface bond shear strength using an apparatus to apply torsional loads on a cylindrical specimen is provided. A plurality of slings is wrapped in opposed circular directions around the specimen. A connecting bar is coupled to a first end of each of the slings. A second end of each of the slings is coupled to a frame. A conventional compression load testing machine applies a compressive load to the connecting member causing the slings to apply rotational forces to the specimen in opposite senses creating torsional stresses. Rotational forces are transmitted to the cylindrical specimen due to friction between the slings and the surface of the specimen being tested. The amount of force applied to the specimen is measured so that the torsional strength of different specimens can be compared.

20 Claims, 11 Drawing Sheets

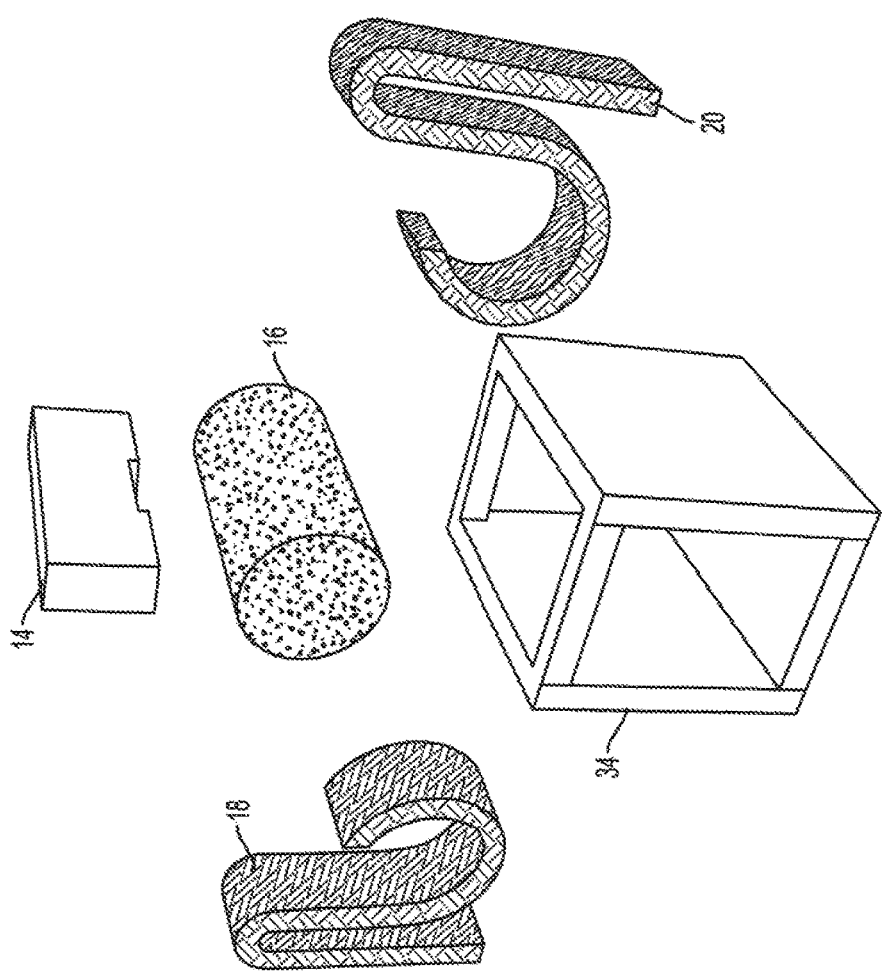

TORSION TESTING DEVICES AND METHODS

CROSS-REFERENCE TO RELATED APPLICATIONS

This invention claims priority to and fully incorporates by reference, provisional patent application Ser. No. 62/427,676 filed on 29 Nov. 2016.

FIELD OF THE INVENTION

This invention relates generally to torsion testing devices and methods. More particularly, it refers to methods, devices and systems for testing the torsional strength, tensile strength, interface shear strength, and shear strength of an essentially cylindrical specimen or cylindrical core, such as for example and without limitation, a cylindrical concrete sample or cylindrical core with a conventional compression load testing machine.

BACKGROUND OF THE INVENTION

One of the main aspects related to structural materials—such as steel, wood, and concrete—is the capability of measuring how the materials will behave under loading. If a material will be used in structural members under compression, the material has to be tested in order to assess how it will behave under compression; if a material will be applied in structural members under bending, a way of measuring the material behavior under bending has to be conceived and used.

Structural materials—such as concrete—are used in structural members acted upon by loadings that will create compression, tensile stresses, bending, shearing stresses, and torsional stresses. Currently, there exist several tests that can be used to test concrete, mortar, and other cement-based materials under compression and bending. For shearing stresses, interface shear in bonded concrete, and helical tensile stresses due to torsional stresses, though, there is no device, method or apparatus to test concrete.

FIGS. 1A through 4B show the tests currently used to assess concrete strength. (1) The first test is the compression test that measures compressive strength of concrete; this test is standardized in the USA—ASTM C39/C39M *Standard Test Method for Compressive Strength of Cylindrical Concrete Specimens*—and in several other countries. (2) The second test is the split tension test used to measure tensile strength of concrete; the method is also standardized in the USA—ASTM C496/C496M *Standard Test Method for Splitting Tensile Strength of Cylindrical Concrete Specimens*—and in other countries. (3) The third test measures flexural strength, or bending strength, of concrete; this test is also defined according to standard procedures in the USA: ASTM C78/C78M and ASTM C293/C293M. (4) The fourth test is referred to as Iosipescu shear test and, although the test is not standardized for concrete, it has been used to measure concrete shear strength; the test is standardized to test composite materials (ASTM D7078/D7078M—*Standard Test Method for Shear Properties of Composite Materials by V-Notched Rail Shear Method*). In all four tests, a universal compression testing machine is used to apply the vertical load downwards.

The inability to assess shear stresses, helical tensile stresses, and shear interface bonding in plain concrete or cored specimens has been a concern of concrete researchers for decades, and the subject is very important to analyze concrete strength and behavior in structural members, and also to evaluate concrete bonding in concrete interfaces. What is needed then are devices and methods for testing concrete shear strength, concrete tensile strength, and concrete shear bonding using torsional stresses in a specimen, for example and without limitation, a cylindrical concrete specimen, or a cored cylinder extracted from a concrete structural member.

SUMMARY OF THE INVENTION

Presented herein are methods, devices and systems for testing the tensile strength in cylinders (helical tensile strength), shear strength in notched cylinders, shear bonding between two materials, and shear strength in unnotched cylindrical specimens using torsional strength of a cylindrical specimen, such as for example and without limitation, a cylindrical concrete sample, or a cylindrical concrete core. In one aspect, the torsional testing device comprises at least one of a plurality of slings, a connecting member that couples an end of each of the slings together, and a means of supporting the slings.

In one aspect, the slings be configured to wrap around at least a portion of an outer perimeter of the specimen in opposed circular directions. That is, a first sling of the plurality of slings can wrap around the specimen in a first circular direction and a second sling of the plurality of slings can wrap around the specimen in a second circular direction that is opposed to the first direction.

The connecting member can be securely attached to a first end of each sling, and a second end of each sling can be securely attached to the means for supporting the slings, such as a frame. The slings can have a sling length such that, when attached to the connecting member and the frame, the specimen is fully supported by the slings.

In use, a conventional compression load testing machine can apply a compressive load to the connecting member. This compressive load causes the slings to apply rotational forces (torques) to the specimen in opposite senses creating torsional stresses. Rotational forces are transmitted to the cylindrical specimen due to friction between the slings and the surface of the specimen being tested. The amount of force applied to the specimen can be measured so that the torsional strength of different specimens can be compared, and the helical tensile strength, shear strength, or shear bonding can be calculated.

The apparatus can be used in conjunction with common uniaxial compression loading machines. The device is comprised of two connected mesh slings (that can be metallic or non-metallic) applied in opposite circular directions around the essentially cylindrical material to be tested. A vertical load is applied in such a way that the slings apply rotational forces (torques) to the essentially cylindrical specimen in opposite directions creating, therefore, increasing torsional stresses. Torsional forces are transmitted to the cylindrical specimen due to friction between the slings and the surface of the material being tested, the magnitude of the friction and the magnitude of the applied torsion grow according to the externally applied load from the uniaxial compression machine.

The apparatus can test essentially cylindrical specimens made of any material, including but not limited to, granular materials such as concrete, mortar, and any cement-based granular material. In addition, the apparatus can be used to apply torsion to any standardized concrete cylinder dimension; hence, the same concrete specimens already commonly used in concrete industry for standard compression (direct uniaxial compression) and tension tests (split tension tests) can now also be used for tests in torsion.

Related methods of operation are also provided. It should be noted that any uniaxial loading machine can be used with this invention and that specimens can very easily be inserted and removed.

The new apparatus can be used to test concrete tensile, bonding strength between concretes, and concrete shear strength. The helical tensile strength can replace splitting tensile and flexural strength. The antiplane shear strength can be used to test: (1) concrete shear (using notched or unnotched cylindrical specimens); and (2) interface bond shear strength in concrete repairs.

In this application, shear strength of concrete, mode III fracture, or antiplane shear, is determined using essentially cylindrical specimens with and without circular notches. For the notched specimens, the apparatus is used with a gap between the parallel wire mesh slings. The notch induces a concentration of shear stresses and the failure of the specimen in the antiplane shear. For the unnotched specimens, the testing is performed with no gap between the mesh slings. This configuration induces a concentration of shear stresses due to the slings' position, leading to shear fracture.

Other apparatuses, methods, systems, features, and advantages of the torsional testing device and the method of its use will be or become apparent to one with skill in the art upon examination of the following figures and detailed description. It is intended that all such additional apparatuses, methods, systems, features, and advantages be included within this description, be within the scope of the torsional testing device and the method of its use, and be protected by the accompanying claims.

BRIEF DESCRIPTION OF THE FIGURES

The accompanying drawings, which are incorporated in and constitute a part of this specification, illustrate certain aspects of the instant invention and together with the description, explain, without limitation, the principles of the invention. Like reference characters used therein indicate like parts throughout the several drawings.

FIG. 5 is an exploded view of the torsion test apparatus illustrating wire mesh slings, steel frame, steel bar with rectangular cross-section and concrete cylindrical specimen;

DETAILED DESCRIPTION OF THE INVENTION

Figure 4A:
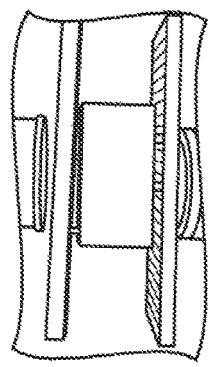
FIG. 4A is an illustration of a prior art Iosipescu shear test on a concrete sample.
Figure 4B:
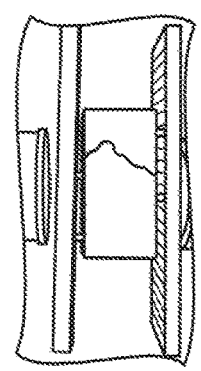
FIG. 4B is an illustration of a failed concrete sample of FIG. 4A.
Figure 3A:
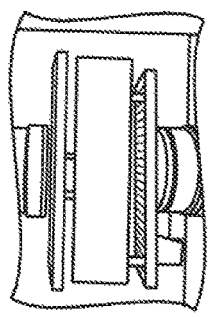
FIG. 3A is an illustration of a prior art flexural strength test to measure the bending strength of a concrete sample.
Figure 3B:
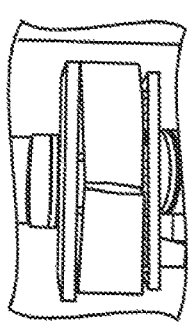
FIG. 3B is an illustration of a failed concrete sample of FIG. 3A.
Figure 2A:
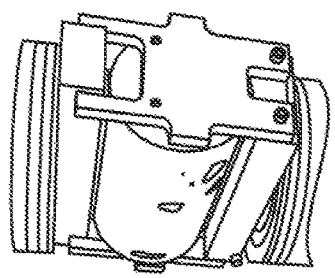
FIG. 2A is an illustration of a prior art split tension test to measure tensile strength of a concrete sample.
Figure 2B:
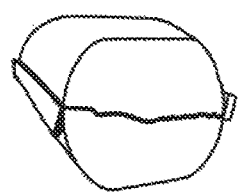
FIG. 2B is an illustration of a failed concrete specimen of FIG. 2A.
Figure 1B:
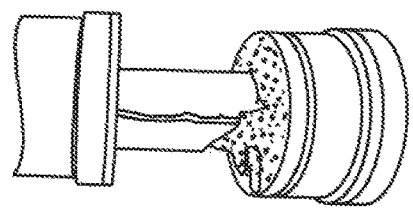
FIG. 1B is an illustration of a failed concrete sample of FIG. 1A.
Figure 1A:
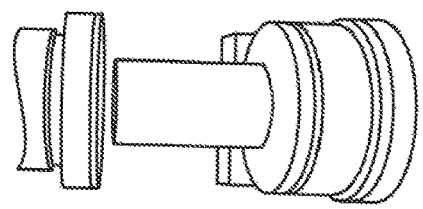
FIG. 1A is a prior art compression test to measure the compressive strength of a concrete sample.
Figure 6:
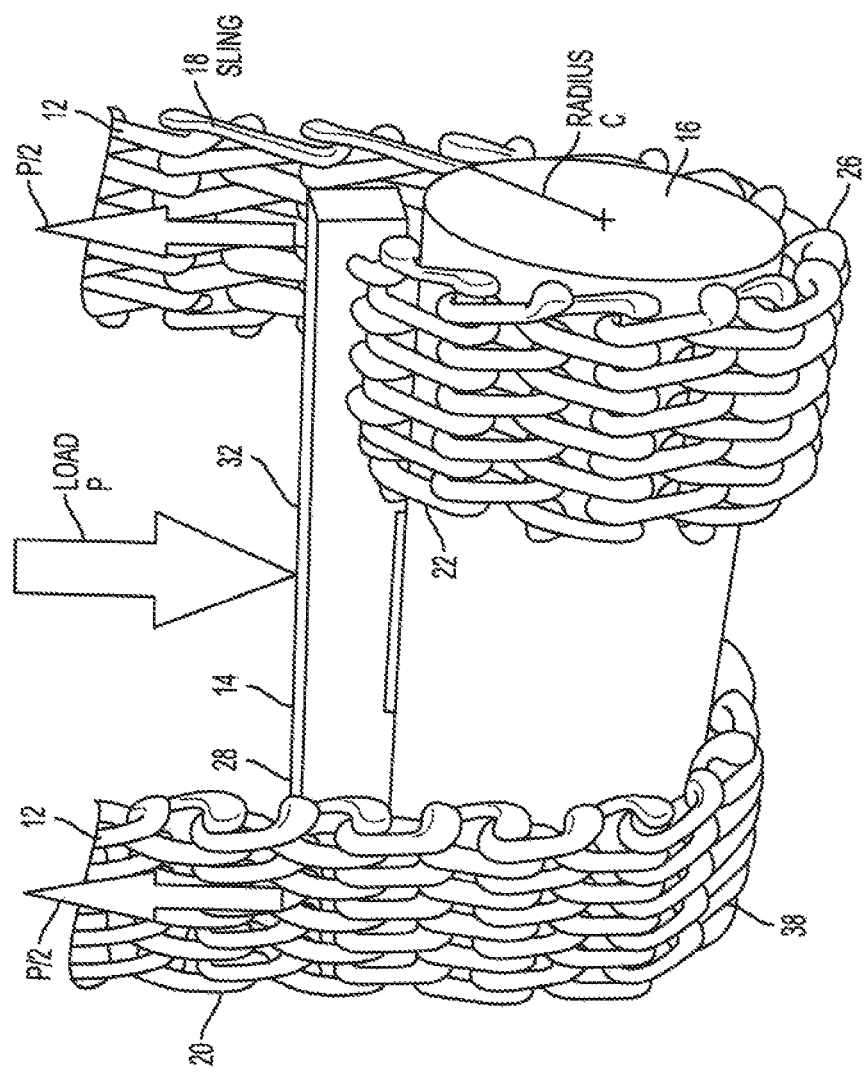
FIG. 6 is a perspective view of the torsional testing device of the present application, showing a specimen supported by a plurality of slings, according to one aspect.
Figure 7:
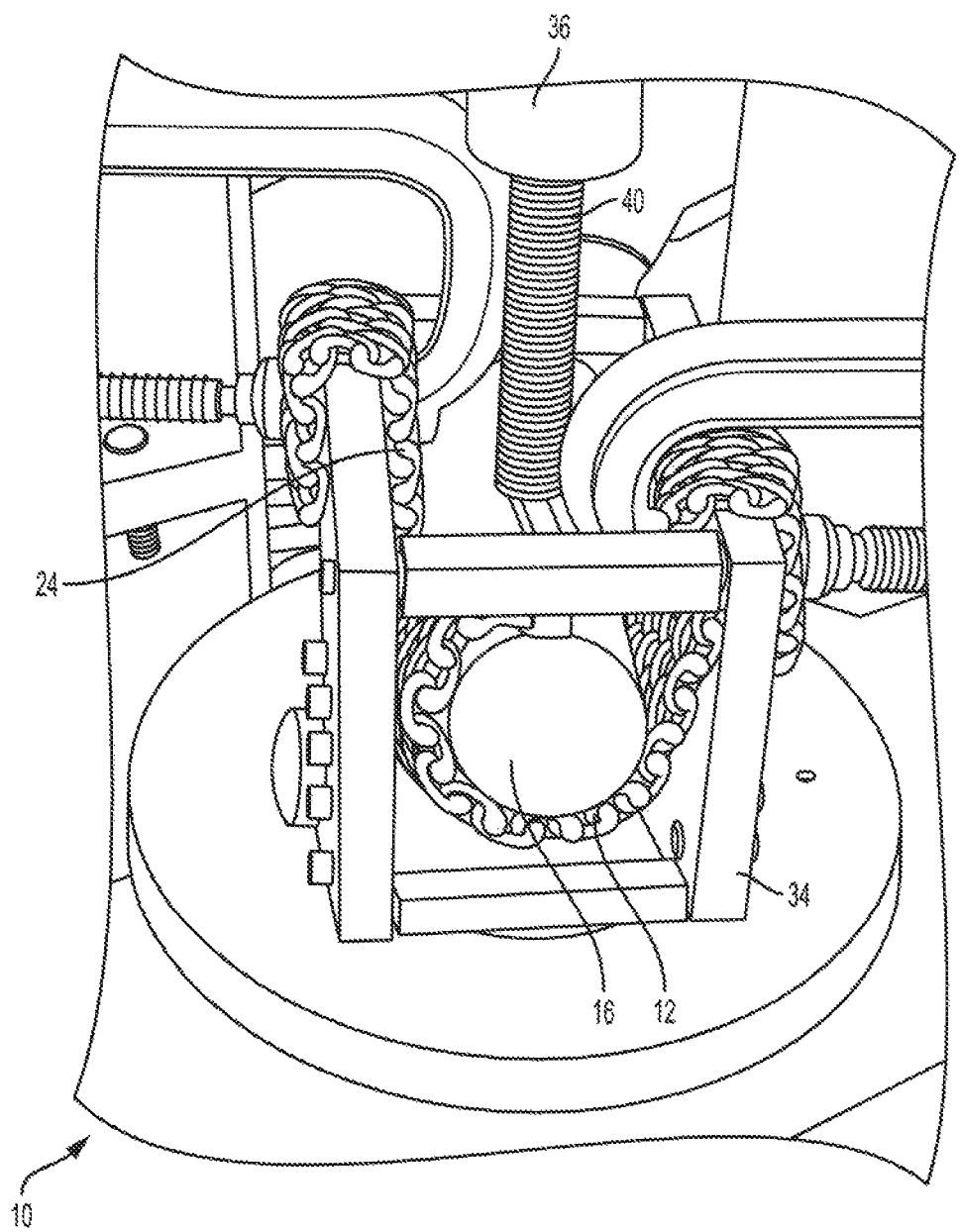
FIG. 7 is a perspective view of the torsional testing device of FIG. 6, in which a concrete compression testing machine is applying a load to the device.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "sling" includes aspects having two or more slings unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Presented herein is a torsional testing device that allows direct application of torsion in cylindrical specimens of any material using a conventional compression load testing machine. In one aspect, the device can apply torsional forces to the specimen to test torsional stresses in the specimen.

As used herein, Applied torque may be calculated by at least the formula:

$$T = \frac{P}{2}c$$

As used herein helical tensile strength, helical tensile stress, shear strength, shear stress, interface strength, and interface stress may be calculated by at least the formula:

$$\tau_{max} = \frac{Tc}{J}$$

$$J = \frac{\pi c^4}{2}$$

$$\tau_{max} = f_{helical} = f_{tensile} = \tau_{shear} = \tau_{interface} = \frac{P}{2} c \cdot c \cdot \frac{2}{\pi c^4} = \frac{P}{\pi c^2}$$

With reference to FIGS. 6-10, the torsional testing device 10 comprises at least a plurality of slings 12 and a connecting member 14 that couples a portion of the plurality of slings together.

The plurality of slings 12 can each be a configured to wrap around a portion of a perimeter of a specimen 16. For example, the sling can be a mesh metallic sling formed with a chain-like structure. Optionally, the sling 12 can be a strap or belt formed from a polymeric material like nylon and the like, or a natural material such as leather. That is, the slings can be an element flexible in two dimensions and having a fixed length, such as a chain, belt and the like. As used herein, the term "sling" means any device having a fixed length capable of wrapping around at least a portion of the specimen such that the sling can frictionally engage the specimen.

In one aspect, the plurality of slings 12 can have a sling width. For example, the sling width can be selected so that a predetermined portion of the specimen 16 is engaged by the slings. In another aspect, the plurality of slings has a sling length selected so that, when wrapped around the specimen as described below, the specimen 16 can be supported by the slings 12. In a further aspect, the plurality of slings has a first end 22, a second end 24 and a central portion 26 extending between the first end and the second end. Optionally, the plurality of slings comprises at least a first sling 18 and a second sling 20.

The connecting member 14 can be an elongate rigid member having a distal end 28, a proximal end 30 and a central portion 32 extending between the distal end and the proximal end. The connecting member can be formed from a metallic material, such as, for example and without limitation, steel. In one aspect, the connecting member 14 can be sized so that the connecting member is not deformable under a testing load, described more fully below.

In one aspect, the torsional testing device 10 can further comprise a frame 34. The frame can be a rigid structure having a frame height greater than the diameter of the specimen 16, so that when in use as described below, the slings 12 can hang from the frame with the specimen fully supported by the slings (that is, so the specimen 16 does not touch any portion of the frame or a testing machine 36). In another aspect, the frame 34 can be sized so that the frame is not deformed under a testing load, described more fully below.

To assemble the torsional testing device 10, the first end 22 of the first sling 18 can be securely attached to the proximal end 30 of the connecting member 14, and the first end of the second sling 20 can be securely attached to the distal end 28 of the connecting member. In one aspect, the slings 12 can be securely attached to the connecting member 14 by welding them together. Other attachment means between the slings and the connecting member, such as a pinned connection, bonding, clamping, sewing and the like are also contemplated. In one aspect, the second end 24 of the first sling 18 can be securely attached to a portion of the frame 34, and the second end of the second sling 20 can be securely attached to a portion of the frame. The slings 12 can be securely attached to the frame by welding them together. Other attachment means between the slings and the frame 34, such as bonding, clamping, sewing and the like are also contemplated.

In use, the connecting member 14 can be positioned on an outer perimeter surface 38 of the specimen 16 and the slings 12 can be wrapped around at least a portion of the specimen in opposed circular directions. That is, the first sling 18 can be wrapped around at least a portion of the specimen in a clockwise direction, and the second sling 20 can be wrapped around at least a portion of the specimen 16 in a counter-clockwise direction. Optionally, this can be reversed so that the first sling 18 can be wrapped around at least a portion of the specimen in a counter-clockwise direction, and the second sling 20 can be wrapped around at least a portion of the specimen 16 in a clockwise direction.

In one aspect, each sling 12 can be wrapped around a portion of the perimeter of the specimen 16 subtended by a predetermined angle. The predetermined angle can be, for example, an angle of about 10°, about 20°, about 30°, 40°, about 45°, about 50°, about 60°, 70°, about 80°, about 90°, about 100°, 110°, about 120°, about 130°, about 135°, 140°, about 150°, about 160°, about 170°, 180°, about 190°, about 200°, about 210°, 220°, about 225°, about 230°, about 240°, 250°, about 260°, about 270°, about 280°, about 290°, about 300°, about 310°, about 315°, about 320°, about 330°, about 340°, about 350°, about 360°, or any other desired angle. In another example, the predetermined angle can be 360°, plus an additional amount. Thus, in one aspect, each sling 12 can be wrapped around a portion of the perimeter of the specimen 16. In another aspect, each sling can be wrapped around the entire perimeter of the specimen. In still another aspect, each sling 12 can be wrapped around the perimeter of the specimen 16 more than one time. For example, each sling can be wrapped around the perimeter of the specimen multiple times.

In a further aspect, each of the first sling 18 and the second sling 20 can be wrapped around the perimeter of the specimen 16 the same amount. Alternatively, the first sling can be wrapped around the specimen a different amount than the second sling. For example, the first sling 18 can be wrapped around the specimen 16 a first distance and the second sling 20 can be wrapped around the specimen 16 a second distance that is greater than or less than the first distance. Each sling 12 can have a sling length so that, when the second end 24 of each sling is securely attached to the frame 34 or other rigid structure, the specimen is suspended by the slings. That is, the specimen 16 can hang from the slings 12.

The torsional testing device 10 with the specimen 16 loaded in the slings 12 as described above can be positioned on a conventional compression load testing machine 36 such that the connecting member 14 is positioned between the specimen 16 and the force applicator 40. Compressive load is applied from the testing machine in such a way that the slings 12 can apply rotational forces (torques) to the specimen 16 in opposite senses creating, therefore, increasing torsional stresses. That is, rotational forces from the first sling 18 can be applied to the specimen in a first rotational direction, and rotational forces from the second sling can be applied to the specimen 16 in a second rotational direction that is opposed to the first rotational direction. Torsional forces can be transmitted to the cylindrical specimen due to friction between the slings 12 and the surface of the specimen being tested. The magnitude of the friction and the magnitude of the applied torsion can grow according to the externally applied load from the compression testing machine 34. This friction created follows approximately Eytelwein's formula (belt friction formula or capstan formula) and, as the downward central load grows, symmetrical axial torsional force develops in the specimen due to the tensioned slings 12.

Figure 8:
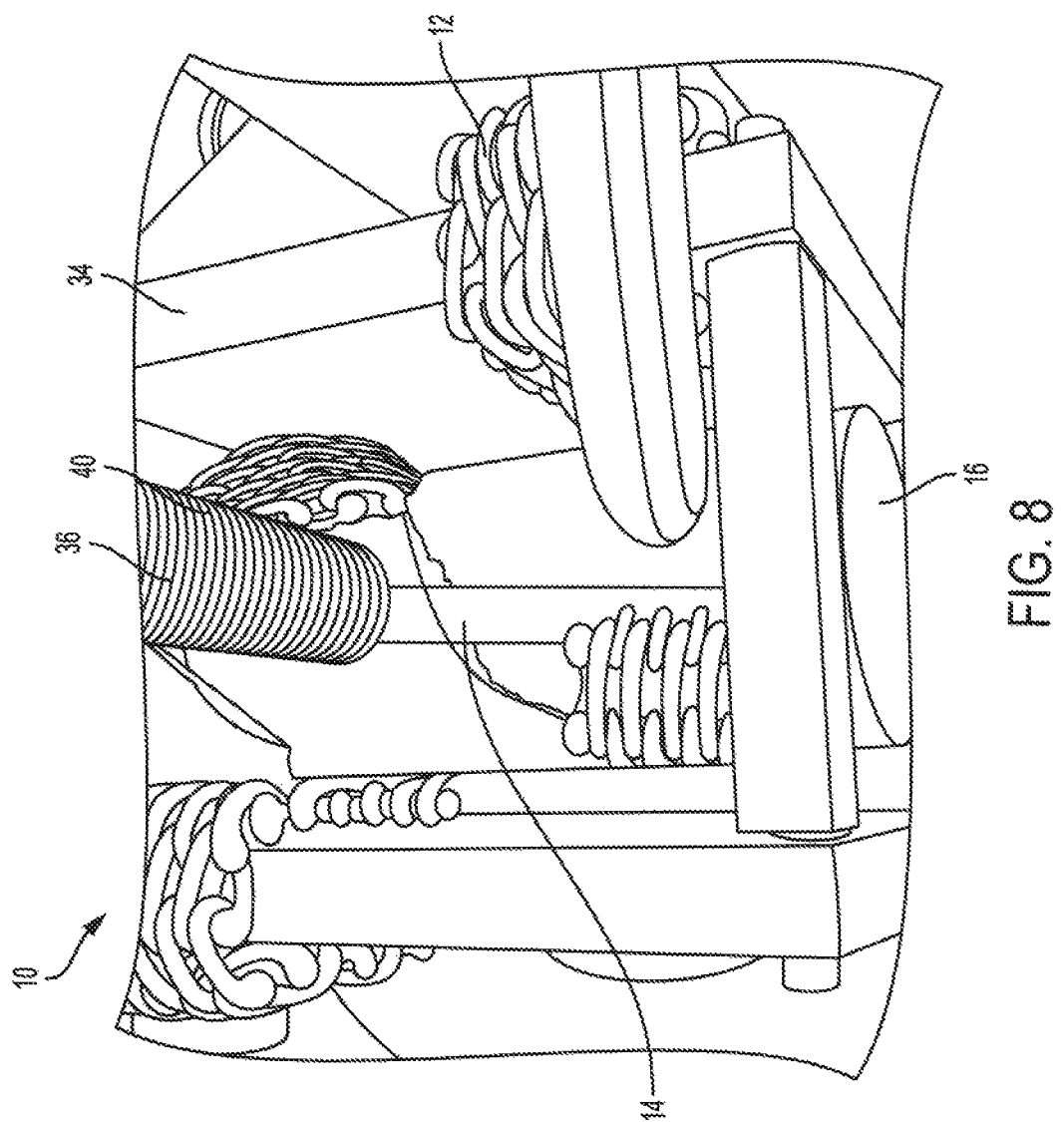
FIG. 8 is a perspective view of the torsional testing device of FIG. 6, in which a specimen has been tested to failure and wherein the specimen failed under helical tensile stress due to the applied torsion.
Figure 9:
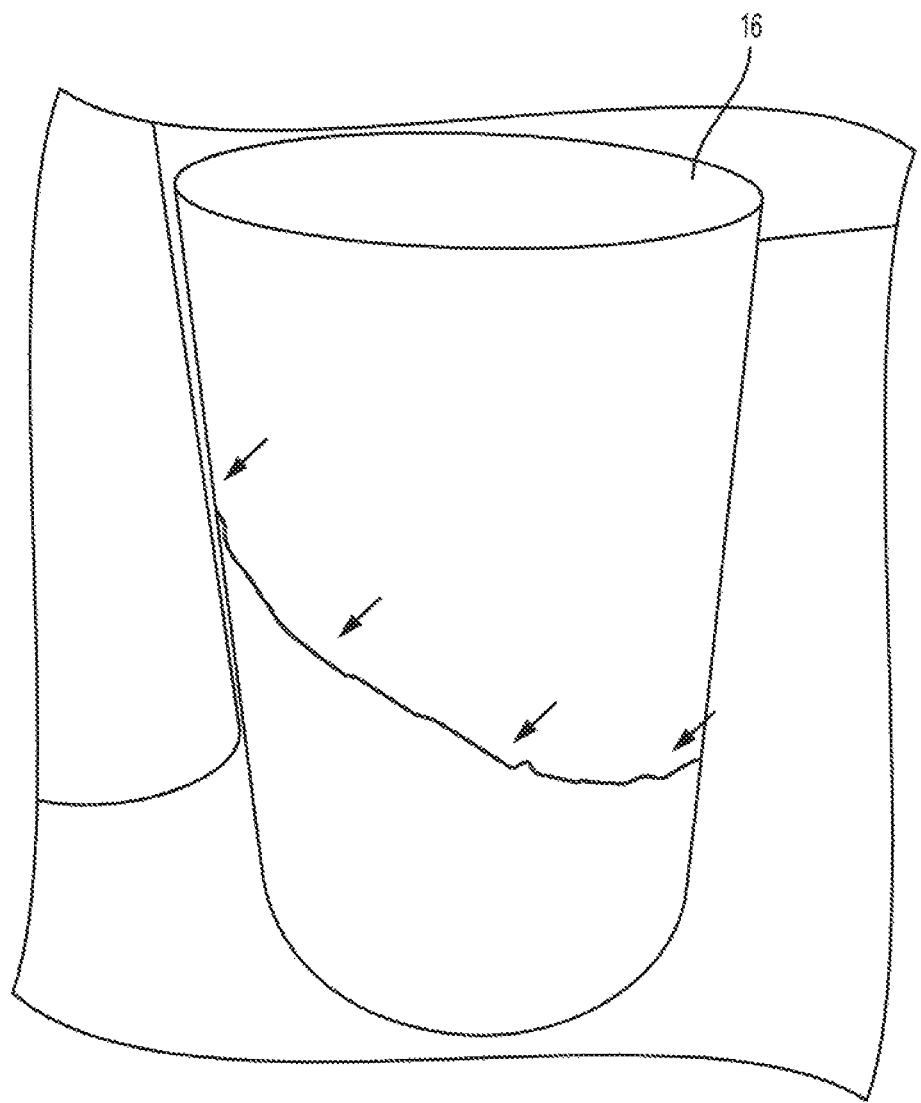
FIG. 9 is a perspective view of the specimen of FIG. 8 where the helical tensile failure is shown.

The amount of force applied to the specimen 16 can be measured so that the torsional strength of different specimens can be compared. For example, the force required to cause failure among different specimens can be compared. In one aspect, the symmetrical torsional forces applied can induce a helical failure of the specimen (this brittle helix-like failure occur in concrete and mortar due to tensile stresses that develop at 450 of the cylinder axis). As a result, the specimen can fail as shown in FIGS. 8 and 9, with a helix forming at, approximately, 45° of the axial direction—as indicated by the arrows in FIG. 9.

Figure 11:
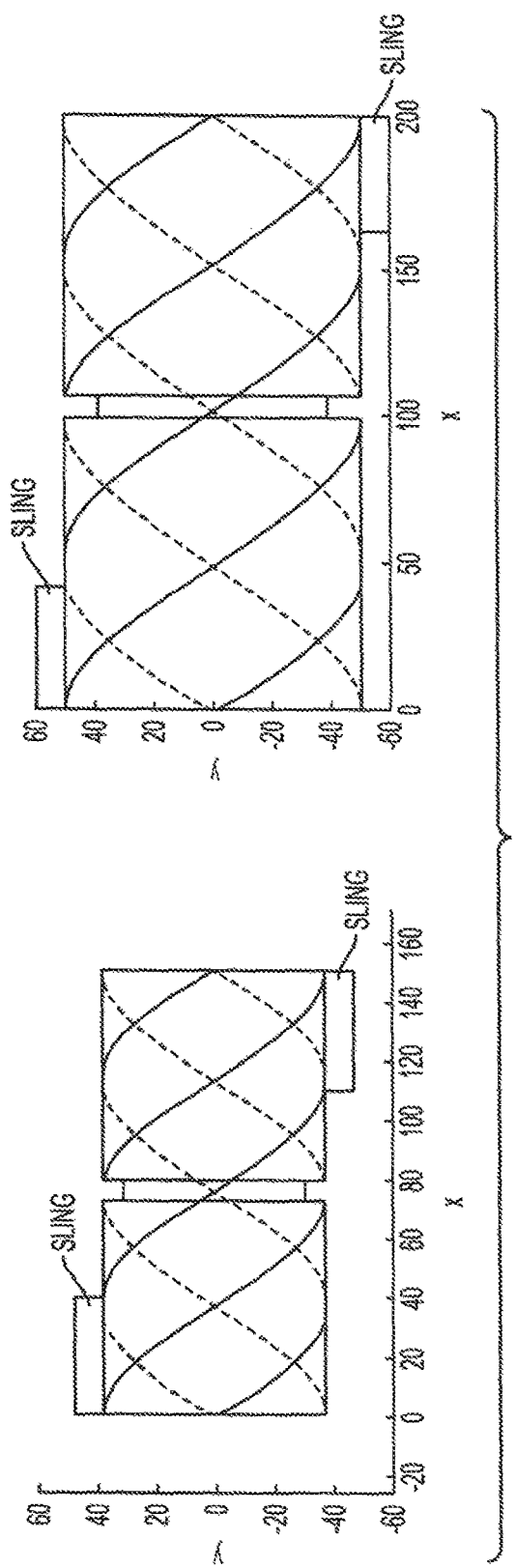
FIG. 11 is a top view of the notched specimens that can be used to test shear strength wherein the notch induces antiplane shear stresses in the plane defined by the circular notch allowing to directly test shear strength.

FIG. 11 illustrates antiplane shear using a notched specimen. The same apparatus and setup can be used to test notched concrete cylindrical specimens as unnotched specimens. With the circular notches, stresses are concentrated in the notched circular section and antiplane shear occurs. This can be used to analyzed mode III fracture (antiplane shear fracture).

Figure 12:
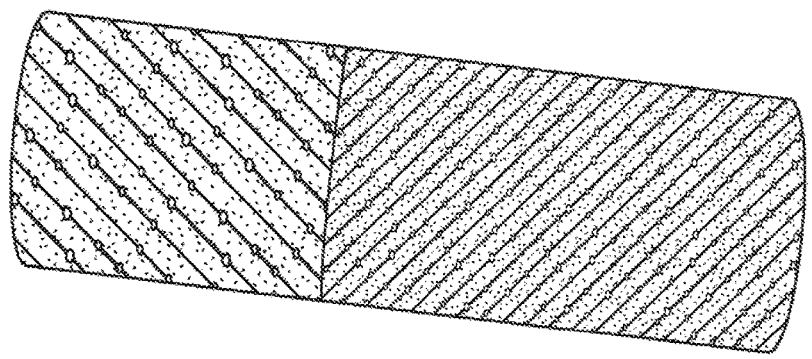
FIG. 12 is a perspective view of cored specimens made of two concrete types bonded at the interface, and wherein the apparatus can be used to measure the interface shear strength between the two different concretes.

As illustrated in FIG. 12, the shear strength of bonded concrete can also be measured to measure the interface bond in concrete repairs. The wire mesh slings can be adjusted to the core sizes and the cores can be tested using the same approach as the previously described cylindrical specimens.

Figure 13A:
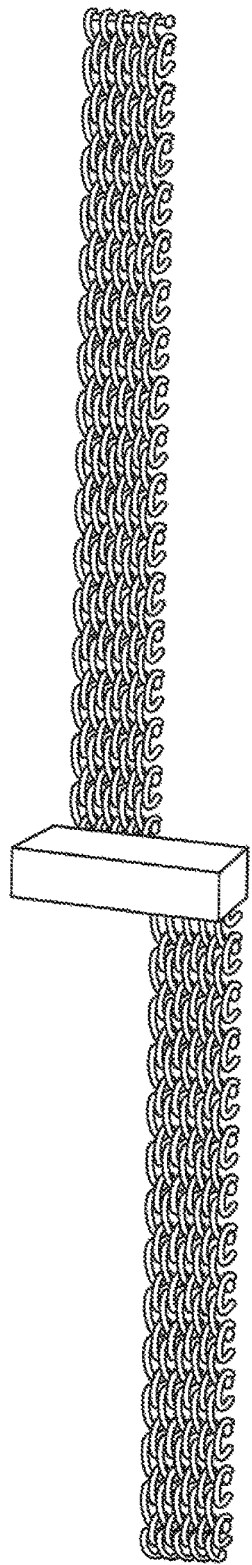
FIGS. 13A and 13B are perspective views of the two configurations for the wire mesh slings: without a gap between the wire mesh slings and with a gap between the wire mesh slings and for which the unnotched specimens—the testing is performed with a gap between the parallel wire mesh slings for notched specimens, and the testing is performed without a gap between the parallel wire mesh slings for unnotched specimens.
Figure 13B:
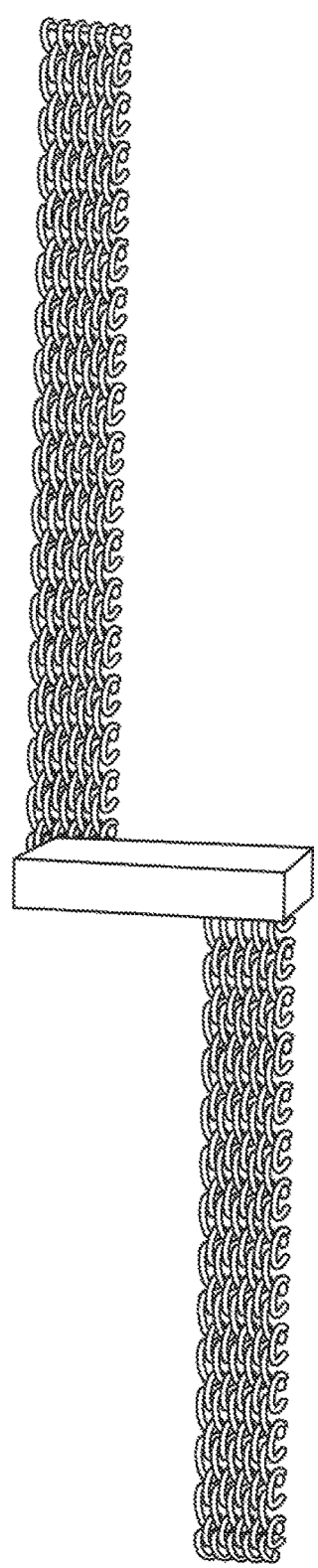
Figure 14:
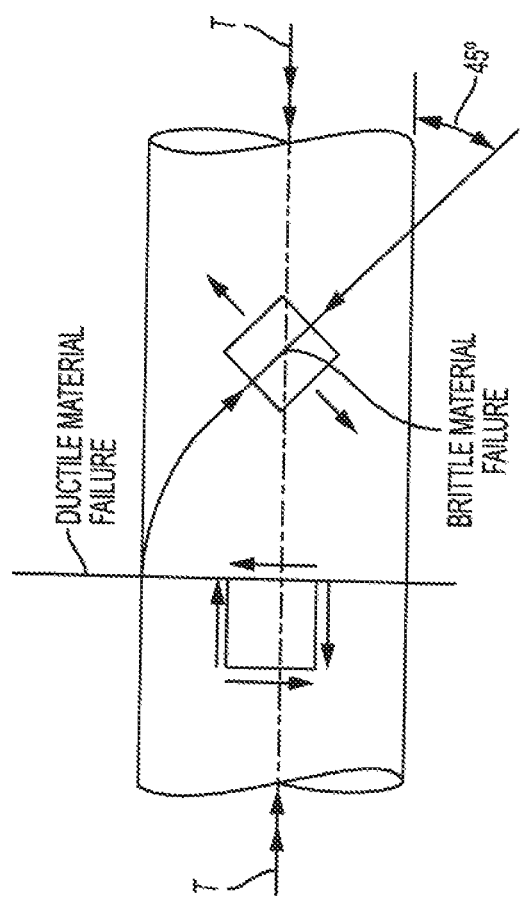
FIG. 14 is an illustration of potential torsional failure surfaces, a pure shear (Mode III) failure in ductile materials; and a tensile (Mode I) failure in brittle materials, e.g., concrete, mortar, and plaster of Paris.

The type of measured shear focuses on whether there is a "gap" between the slings as better illustrated in FIGS. 13A and 13B. If no "gap" exists between the mesh slings, FIG. 13A, i.e., the lower edge of the upper mesh sling is aligned with the upper edge of the lower mesh sling, antiplane shear can be applied in unnotched or notched cylindrical specimens. With a "gap" between the slings, FIG. 13B, helical tensile strength, shear strength and interface shear strength between bonded layers is measured.

The torsional testing device 10 can be applied to cylindrical specimens made of any material, including granular materials such as concrete, mortar, and any cement-based granular material. In addition, the device can be used to apply torsion to any standardized concrete cylinder dimension; hence, the same concrete specimens already commonly used in concrete industry for standard compression (direct uniaxial compression) and tension tests (splitting tension tests) can now also be used for tests in torsion. That is, the torsional testing device allows a direct measurement of concrete helical tensile strength, and shear strength (in notched and unnotched specimens) using standardized concrete cylindrical specimen: 3×6 in. (75×150 mm), 4×8 in. (100×200 mm), or 6×12 in. (150×300 mm) for example. The testing device also allows a direct measurement of shear strength in interfaces of bonded concrete layers using cylindrical cored specimens.

Figure 10:
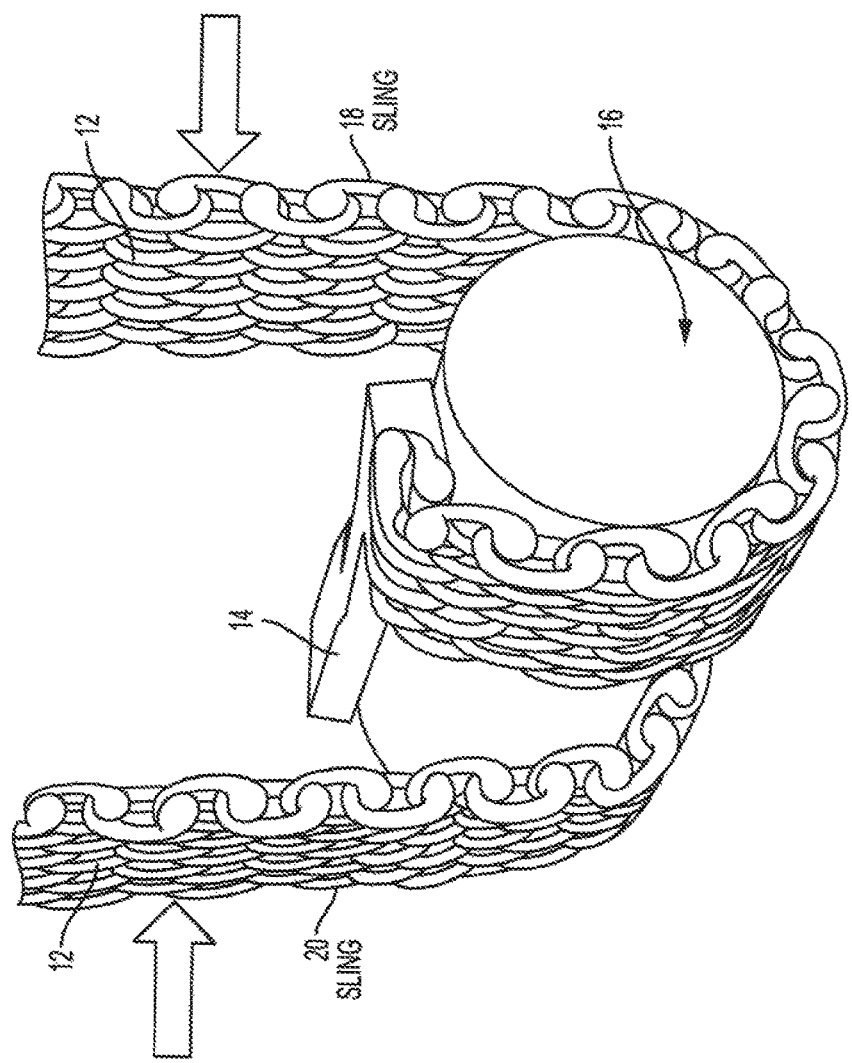
FIG. 10 is a perspective view of the torsional testing device of FIG. 6, in which alternate force arrows are illustrated and wherein the arrows indicate the application of loads using bars or other parts, such as elongated metallic members, to apply the torque and to create the stresses to measure the helical tensile strength, shear strength, or bonding strength.

In another aspect, alternatively, in use, a load can be applied to a portion of the slings 12 in a direction tangent to the specimen 16, as illustrated by the arrows in FIG. 10. In this aspect, force need not be applied to the connecting member 14 by the testing machine. Instead, the tangential force applied to the slings can cause the slings 12 to apply rotational forces (torques) to the specimen 16 in opposite senses creating increasing torsional stresses as described above.

In the following table, mixtures are indicated in the first column ("Mix."), Mix. 1 is plaster of Paris, and Mix. 2, 3, 4, 5, and 6 are concretes with different strengths ($f_c$). Sample numbers are in the second column ("Sample") and the type of material is also indicated: plaster or concrete (third column—"Type"). The nominal sizes of the cylinders used in the tests, diameter and length, in millimeters are listed in column "nom. Size (mm)". Strength of concretes, for each concrete mixture, is indicated in Megapascals (MPa), column "$f_c$ (MPa)". Applied loads "P" in the tests, in kN, and the type of test, tensile or antiplane shear, are also indicated: columns "Applied load" and "Type of test". The real measured radius "c" of each cylinder tested, in millimeters, is also indicated. From the radius, the polar moment of inertia of the circular cross section "J" can be calculated: $J=0.5 (\pi) c^4$. With the applied load "P" and the radius of each specimen the torque 'T' is computed $T=0.5$ P c. The maximum stress, tensile helical or antiplane shear, can be calculated: $f_{helical}=f_{tensie}=f_{shear}=T\ c/J=0.5\ P\ c\cdot c/(0.5\ \pi c^4)=P/(\pi c^2)$—column "Max. stress $f_{hel}$ (MPa)". For the concrete mixtures, the results are also indicated as a percentage of the concrete compressive strength, column "% $f_c$". Mean values, standard deviation, and coefficient of variation for each mix are indicated in the last three columns. Mixture 6, samples 66 to 75, were tested under antiplane shear (no gap between the slings, FIG. 13A: samples 66 to 70) and helical tensile (samples 71 to 75) stresses.

TABLE I (Results obtained with 75 tests with plaster of Paris (samples 1-5) and concrete (samples 6-75) specimens.)

| Mix. | Sample | Type | nom. size (mm) | $f_c$ (MPa) | Applied load - P (kN) | Type of test | Radius c (mm) | J (mm$^4$) | Torque (kN · mm) |
|---|---|---|---|---|---|---|---|---|---|
| 1 | 1 | plaster | 75 × 150 | — | 8.28 | tensile | 38.5 | 3.451E+06 | 159.448 |
|  | 2 |  | 75 × 150 |  | 8.62 |  | 38.5 | 3.451E+06 | 165.993 |
|  | 3 |  | 75 × 150 |  | 8.67 |  | 38.5 | 3.451E+06 | 166.840 |
|  | 4 |  | 75 × 150 |  | 8.99 |  | 38.5 | 3.451E+06 | 173.135 |
|  | 5 |  | 75 × 150 |  | 9.25 |  | 38.5 | 3.451E+06 | 178.005 |
| 2 | 6 | concr. | 75 × 150 | 38.40 | 19.67 | tensile | 38.5 | 3.451E+06 | 378.667 |
|  | 7 |  | 75 × 150 |  | 19.84 |  | 38.5 | 3.451E+06 | 381.939 |
|  | 8 |  | 75 × 150 |  | 20.45 |  | 38.5 | 3.451E+06 | 393.566 |
|  | 9 |  | 75 × 150 |  | 20.69 |  | 38.5 | 3.451E+06 | 398.321 |
|  | 10 |  | 75 × 150 |  | 22.34 |  | 38.5 | 3.451E+06 | 429.968 |
|  | 11 |  | 75 × 150 |  | 22.72 |  | 38.5 | 3.451E+06 | 437.341 |
|  | 12 |  | 75 × 150 |  | 23.39 |  | 38.5 | 3.451E+06 | 450.181 |
|  | 13 |  | 100 × 200 |  | 40.72 |  | 50.8 | 1.046E+07 | 1034.237 |
|  | 14 |  | 75 × 150 |  | 24.58 |  | 38.5 | 3.451E+06 | 473.107 |
|  | 15 |  | 75 × 150 |  | 24.58 |  | 38.5 | 3.451E+06 | 473.107 |
|  | 16 |  | 75 × 150 |  | 24.92 |  | 38.5 | 3.451E+06 | 479.787 |
|  | 17 |  | 75 × 150 |  | 25.59 |  | 38.5 | 3.451E+06 | 492.646 |
|  | 18 |  | 75 × 150 |  | 25.71 |  | 38.5 | 3.451E+06 | 494.937 |
|  | 19 |  | 75 × 150 |  | 26.47 |  | 38.5 | 3.451E+06 | 509.471 |
| 3 | 20 | concr. | 75 × 150 | 43.40 | 17.47 | tensile | 38.5 | 3.451E+06 | 336.240 |
|  | 21 |  | 75 × 150 |  | 18.21 |  | 38.5 | 3.451E+06 | 350.466 |
|  | 22 |  | 75 × 150 |  | 19.26 |  | 38.5 | 3.451E+06 | 370.794 |
|  | 23 |  | 75 × 150 |  | 19.82 |  | 38.5 | 3.451E+06 | 381.554 |
|  | 24 |  | 75 × 150 |  | 19.89 |  | 38.5 | 3.451E+06 | 382.844 |
|  | 25 |  | 75 × 150 |  | 20.63 |  | 38.5 | 3.451E+06 | 397.166 |
|  | 26 |  | 75 × 150 |  | 20.75 |  | 38.5 | 3.451E+06 | 399.361 |
|  | 27 |  | 75 × 150 |  | 21.00 |  | 38.5 | 3.451E+06 | 404.250 |
|  | 28 |  | 100 × 200 |  | 36.68 |  | 50.8 | 1.046E+07 | 931.621 |
|  | 29 |  | 75 × 150 |  | 22.74 |  | 38.5 | 3.451E+06 | 437.668 |
|  | 30 |  | 75 × 150 |  | 23.38 |  | 38.5 | 3.451E+06 | 450.065 |
|  | 31 |  | 75 × 150 |  | 23.70 |  | 38.5 | 3.451E+06 | 456.302 |
|  | 32 |  | 75 × 150 |  | 24.41 |  | 38.5 | 3.451E+06 | 469.873 |
|  | 33 |  | 75 × 150 |  | 24.56 |  | 38.5 | 3.451E+06 | 472.799 |
|  | 34 |  | 75 × 150 |  | 24.65 |  | 38.5 | 3.451E+06 | 474.474 |
|  | 35 |  | 75 × 150 |  | 24.67 |  | 38.5 | 3.451E+06 | 474.936 |
|  | 36 |  | 75 × 150 |  | 24.68 |  | 38.5 | 3.451E+06 | 474.994 |
|  | 37 |  | 75 × 150 |  | 24.71 |  | 38.5 | 3.451E+06 | 475.648 |
|  | 38 |  | 75 × 150 |  | 24.90 |  | 38.5 | 3.451E+06 | 479.344 |
|  | 39 |  | 75 × 150 |  | 25.08 |  | 38.5 | 3.451E+06 | 482.829 |
|  | 40 |  | 100 × 200 |  | 43.98 |  | 50.8 | 1.046E+07 | 1117.041 |
|  | 41 |  | 75 × 150 |  | 25.50 |  | 38.5 | 3.451E+06 | 490.914 |
|  | 42 |  | 75 × 150 |  | 25.87 |  | 38.5 | 3.451E+06 | 498.055 |
|  | 43 |  | 75 × 150 |  | 26.63 |  | 38.5 | 3.451E+06 | 512.589 |
|  | 44 |  | 75 × 150 |  | 26.63 |  | 38.5 | 3.451E+06 | 512.705 |
|  | 45 |  | 75 × 150 |  | 27.00 |  | 38.5 | 3.451E+06 | 519.692 |
|  | 46 |  | 75 × 150 |  | 28.60 |  | 38.5 | 3.451E+06 | 550.492 |
|  | 47 |  | 75 × 150 |  | 28.74 |  | 38.5 | 3.451E+06 | 553.187 |
|  | 48 |  | 75 × 150 |  | 29.26 |  | 38.5 | 3.451E+06 | 563.332 |
|  | 49 |  | 75 × 150 |  | 29.53 |  | 38.5 | 3.451E+06 | 568.453 |
| 4 | 50 | concr. | 75 × 150 | 44.30 | 16.03 | tensile | 38.5 | 3.451E+06 | 308.539 |
|  | 51 |  | 75 × 150 |  | 17.12 |  | 38.5 | 3.451E+06 | 329.599 |
|  | 52 |  | 75 × 150 |  | 19.18 |  | 38.5 | 3.451E+06 | 369.157 |
|  | 53 |  | 75 × 150 |  | 22.25 |  | 38.5 | 3.451E+06 | 428.351 |
|  | 54 |  | 75 × 150 |  | 22.73 |  | 38.5 | 3.451E+06 | 437.572 |
|  | 55 |  | 100 × 200 |  | 39.63 |  | 50.8 | 1.046E+07 | 1006.704 |
| 5 | 56 | concr. | 75 × 150 | 56.00 | 22.51 | tensile | 38.5 | 3.451E+06 | 414.045 |
|  | 57 |  | 75 × 150 |  | 22.64 |  | 38.5 | 3.451E+06 | 435.801 |
|  | 58 |  | 75 × 150 |  | 27.82 |  | 38.5 | 3.451E+06 | 535.535 |
|  | 59 |  | 75 × 150 |  | 28.12 |  | 38.5 | 3.451E+06 | 541.291 |
|  | 60 |  | 75 × 150 |  | 28.27 |  | 38.5 | 3.451E+06 | 544.121 |
|  | 61 |  | 75 × 150 |  | 28.73 |  | 38.5 | 3.451E+06 | 552.976 |
|  | 62 |  | 75 × 150 |  | 28.88 |  | 38.5 | 3.451E+06 | 555.921 |
|  | 63 |  | 75 × 150 |  | 29.93 |  | 38.5 | 3.451E+06 | 576.210 |
|  | 64 |  | 100 × 200 |  | 52.76 |  | 50.8 | 1.046E+07 | 1340.079 |
|  | 65 |  | 75 × 150 |  | 31.23 |  | 38.5 | 3.451E+06 | 601.120 |
| 5 | 66 | concr. | 75 × 150 | 44.29 | 24.21 | antiplane | 38.1 | 3.310E+06 | 461.120 |
|  | 67 |  | 75 × 150 |  | 24.60 |  | 38.1 | 3.310E+06 | 468.667 |
|  | 68 |  | 75 × 150 |  | 24.74 |  | 38.1 | 3.310E+06 | 471.239 |
|  | 69 |  | 75 × 150 |  | 25.77 |  | 38.1 | 3.310E+06 | 490.835 |
|  | 70 |  | 75 × 150 |  | 30.70 |  | 38.1 | 3.310E+06 | 584.743 |
|  | 71 |  | 75 × 150 |  | 22.54 | tensile | 38.1 | 3.310E+06 | 429.328 |
|  | 72 |  | 75 × 150 |  | 24.62 |  | 38.1 | 3.310E+06 | 468.928 |
|  | 73 |  | 75 × 150 |  | 24.72 |  | 38.1 | 3.310E+06 | 470.950 |

TABLE I-continued (Results obtained with 75 tests with plaster of Paris
(samples 1-5) and concrete (samples 6-75) specimens.)

| | | | | | | |
|---|---|---|---|---|---|---|
| 74 | 75 × 150 | 26.81 | | 38.1 | 3.310E+06 | 510.722 |
| 75 | 75 × 150 | 30.08 | | 38.1 | 3.310E+06 | 572.975 |

| Mix. | Sample | Max. stress $f_{hel.}$ (MPa) | % $f_c$ | Mean | Std. dev. | Coef. var. (%) |
|---|---|---|---|---|---|---|
| 1 | 1 | 1.779 | — | 1.882 | 0.079 | 4.22 |
|   | 2 | 1.852 | — |   |   |   |
|   | 3 | 1.861 | — |   |   |   |
|   | 4 | 1.931 | — |   |   |   |
|   | 5 | 1.986 | — |   |   |   |
| 2 | 6 | 4.224 | 11.00 | 5.009 | 0.519 | 10.36 |
|   | 7 | 4.261 | 11.10 |   |   |   |
|   | 8 | 4.391 | 11.43 |   |   |   |
|   | 9 | 4.444 | 11.57 |   |   |   |
|   | 10 | 4.797 | 12.49 |   |   |   |
|   | 11 | 4.879 | 12.71 |   |   |   |
|   | 12 | 5.022 | 13.08 |   |   |   |
|   | 13 | 5.022 | 13.08 |   |   |   |
|   | 14 | 5.278 | 13.74 |   |   |   |
|   | 15 | 5.278 | 13.74 |   |   |   |
|   | 16 | 5.352 | 13.94 |   |   |   |
|   | 17 | 5.496 | 14.31 |   |   |   |
|   | 18 | 5.521 | 14.38 |   |   |   |
|   | 19 | 5.684 | 14.80 |   |   |   |
| 3 | 20 | 3.751 | 8.64 | 5.144 | 0.703 | 13.67 |
|   | 21 | 3.910 | 9.01 |   |   |   |
|   | 22 | 4.136 | 9.53 |   |   |   |
|   | 23 | 4.257 | 9.81 |   |   |   |
|   | 24 | 4.271 | 9.84 |   |   |   |
|   | 25 | 4.431 | 10.21 |   |   |   |
|   | 26 | 4.455 | 10.27 |   |   |   |
|   | 27 | 4.510 | 10.39 |   |   |   |
|   | 28 | 4.524 | 10.42 |   |   |   |
|   | 29 | 4.883 | 11.25 |   |   |   |
|   | 30 | 5.021 | 11.57 |   |   |   |
|   | 31 | 5.090 | 11.73 |   |   |   |
|   | 32 | 5.242 | 12.08 |   |   |   |
|   | 33 | 5.274 | 12.15 |   |   |   |
|   | 34 | 5.293 | 12.20 |   |   |   |
|   | 35 | 5.298 | 12.21 |   |   |   |
|   | 36 | 5.299 | 12.21 |   |   |   |
|   | 37 | 5.306 | 12.23 |   |   |   |
|   | 38 | 5.347 | 12.32 |   |   |   |
|   | 39 | 5.386 | 12.41 |   |   |   |
|   | 40 | 5.424 | 12.50 |   |   |   |
|   | 41 | 5.477 | 12.62 |   |   |   |
|   | 42 | 5.556 | 12.80 |   |   |   |
|   | 43 | 5.718 | 13.18 |   |   |   |
|   | 44 | 5.720 | 13.18 |   |   |   |
|   | 45 | 5.798 | 13.36 |   |   |   |
|   | 46 | 6.141 | 14.15 |   |   |   |
|   | 47 | 6.171 | 14.22 |   |   |   |
|   | 48 | 6.284 | 14.48 |   |   |   |
|   | 49 | 6.342 | 14.61 |   |   |   |
| 4 | 50 | 3.442 | 7.77 | 4.298 | 0.644 | 14.98 |
|   | 51 | 3.677 | 8.30 |   |   |   |
|   | 52 | 4.118 | 9.30 |   |   |   |
|   | 53 | 4.779 | 10.79 |   |   |   |
|   | 54 | 4.881 | 11.02 |   |   |   |
|   | 55 | 4.889 | 11.04 |   |   |   |
| 5 | 56 | 4.620 | 8.25 | 5.958 | 0.683 | 11.46 |
|   | 57 | 4.862 | 8.68 |   |   |   |
|   | 58 | 5.974 | 10.67 |   |   |   |
|   | 59 | 6.038 | 10.78 |   |   |   |
|   | 60 | 6.070 | 10.84 |   |   |   |
|   | 61 | 6.169 | 11.02 |   |   |   |
|   | 62 | 6.202 | 11.07 |   |   |   |
|   | 63 | 6.428 | 11.48 |   |   |   |
|   | 64 | 6.508 | 11.62 |   |   |   |
|   | 65 | 6.706 | 11.97 |   |   |   |
| 5 | 66 | 5.308 | 11.98 | 5.702 | 0.589 | 10.33 |
|   | 67 | 5.395 | 12.18 |   |   |   |
|   | 68 | 5.424 | 12.25 |   |   |   |
|   | 69 | 5.650 | 12.76 |   |   |   |
|   | 70 | 6.731 | 15.20 |   |   |   |

TABLE I-continued (Results obtained with 75 tests with plaster of Paris
(samples 1-5) and concrete (samples 6-75) specimens.)

| | | | | | |
|---|---|---|---|---|---|
| 71 | 4.942 | 11.16 | 5.647 | 0.625 | 11.07 |
| 72 | 5.398 | 12.19 | | | |
| 73 | 5.421 | 12.24 | | | |
| 74 | 5.879 | 13.27 | | | |
| 75 | 6.595 | 14.89 | | | |

TABLE II (Average properties, statistical analysis, and comparison with the split tension test.)

| MIX. | Type | $f_c$ (MPa) | Type of test | mean $f_{hel.}$ (MPa) | Std. dev. | Coef. var. (%) | $f_{split}$ (MPa) | $f_{hel.}/f_{split}$ (%) |
|---|---|---|---|---|---|---|---|---|
| 1 | plaster | — | tensile | 1.882 | 0.079 | 4.22 | 1.462 | 28.710 |
| 2 | concrete | 38.40 | tensile | 5.009 | 0.519 | 10.36 | 4.186 | 19.660 |
| 3 | concrete | 43.40 | tensile | 5.144 | 0.703 | 13.67 | 3.467 | 48.384 |
| 4 | concrete | 44.30 | tensile | 4.298 | 0.644 | 14.98 | 4.215 | 1.950 |
| 5 | concrete | 56.00 | tensile | 5.958 | 0.683 | 11.46 | 4.530 | 31.524 |
| 6 | concrete | 44.29 | antiplane | 5.702 | 0.589 | 10.33 | 4.117 | 38.496 |
| | | | tensile | 5.647 | 0.625 | 11.07 | | 37.170 |

The above Table lists average properties of the mixtures used in Table I. The splitting tensile strength of each mixture used is also listed—$f_{split}$ (MPa)—and compared to values obtained for helical failure—column "$f_{hel}/f_{split}$ (%)".

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A torsional testing device for an essentially cylindrical sample comprising:
a frame having opposed sides;
at least a first and a second sling supporting at least a portion of the sample at opposed ends of the sample, each of the slings wrapped about at least a portion of the sample in an opposed direction;
a connecting member having a proximal and a distal end and positioned on an outer perimeter surface of the sample;
one first portion of the first sling affixed to the connecting member at the proximal end and one first portion of the second sling affixed to the connecting member at the distal end;
one second portion of the first sling affixed to one side of the box-shaped frame and one second portion of the second sling affixed to an opposed side of the box-shaped frame;
a tangential force applicator normal to a longitudinal axis of the connecting member, the force applicator applying rotational forces to the sample in opposite directions creating increasing torsional stresses to the sample.

2. The torsional testing device of claim 1, wherein the tangential force applicator creates opposed torque on the sample by the application of pressure in a downward direction through the connecting member.

3. The torsional testing device of claim 2, wherein the tangential force applicator is a uniaxial compression loading machine.

4. The torsional testing device of claim 1, wherein the first and second slings are flexible.

5. The torsional testing device of claim 4, wherein the first and second slings are chain-like.

6. The torsional testing device of claim 1, wherein the one first portion of the first sling affixed to the connecting member at the proximal end and the one first portion of the second sling affixed to the connecting member at the distal end are permanently affixed to the connecting member.

7. The torsional testing device of claim 1, wherein the essentially cylindrical sample is concrete.

8. The torsional testing device of claim 1, wherein the first and second slings have a sling length such that when attached to the connecting member and the frame, the sample is fully supported by the slings.

9. The torsional testing device of claim 1, wherein the first and second slings are in contacting engagement about an interior side.

10. The torsional testing device of claim 1, wherein the first and second slings are not in contacting engagement about an interior side.

11. A method of testing an essentially cylindrical sample comprising the steps of:
inserting the essentially cylindrical sample into a torsional testing device; and
applying a tangential force normal to a longitudinal axis of the sample, the tangential force generating rotational forces in the sample in opposite directions creating increasing torsional stresses to the sample, the torsional testing device comprising:

a frame having opposed sides;

at least a first and a second sling supporting at least a portion of the sample at opposed ends of the sample, each of the slings wrapped about at least a portion of the sample in an opposed direction;

a connecting member having a proximal and a distal end and positioned on an outer perimeter surface of the sample;

one first portion of the first sling affixed to the connecting member at the proximal end and one first portion of the second sling affixed to the connecting member at the distal end;

one second portion of the first sling affixed to one side of the box-shaped frame and one second portion of the second sling affixed to an opposed side of the box-shaped frame;

a tangential force applicator normal to a longitudinal axis of the connecting member, the force applicator applying rotational forces to the sample in opposite directions creating increasing torsional stresses to the sample.

12. The method of claim 11, wherein
the tangential force applicator creates opposed torque on the sample by the application of pressure in a downward direction through the connecting member.

13. The method of claim 12, wherein
the tangential force applicator is a uniaxial compression loading machine.

14. The process of claim 11, wherein
the first and second slings are flexible.

15. The process of claim 14, wherein
the first and second slings are chain-like.

16. The process of claim 11, wherein
the one first portion of the first sling affixed to the connecting member at the proximal end and the one first portion of the second sling affixed to the connecting member at the distal end are permanently affixed to the connecting member.

17. The process of claim 11, wherein
the essentially cylindrical sample is concrete.

18. The process of claim 11, wherein
the first and second slings have a sling length such that when attached to the connecting member and the frame, the sample is fully supported by the slings.

19. The process of claim 11, wherein
the first and second slings are in contacting engagement about an interior side.

20. The process of claim 11, wherein
the first and second slings are not in contacting engagement about an interior side.

\* \* \* \* \*